(12) United States Patent
Kreindel

(10) Patent No.: US 11,896,293 B2
(45) Date of Patent: Feb. 13, 2024

(54) NASAL TISSUE TREATMENT METHOD AND RELATED DEVICE

(71) Applicant: INMODE LTD, Yokneam (IL)

(72) Inventor: Michael Kreindel, Richmond Hill (CA)

(73) Assignee: Inmode Ltd., Yokneam (IL)

( * ) Notice: Subject to any disclaimer, the term of this patent is extended or adjusted under 35 U.S.C. 154(b) by 572 days.

(21) Appl. No.: 17/025,510

(22) Filed: Sep. 18, 2020

(65) Prior Publication Data

US 2022/0022949 A1    Jan. 27, 2022

Related U.S. Application Data

(60) Provisional application No. 63/054,437, filed on Jul. 21, 2020.

(51) Int. Cl.
| | |
|---|---|
| *A61B 18/14* | (2006.01) |
| *A61B 18/16* | (2006.01) |
| *A61F 5/08* | (2006.01) |
| *A61B 18/00* | (2006.01) |

(52) U.S. Cl.
CPC .......... *A61B 18/1485* (2013.01); *A61B 18/16* (2013.01); *A61F 5/08* (2013.01); *A61B 2018/00011* (2013.01); *A61B 2018/00327* (2013.01); *A61B 2018/00589* (2013.01); *A61B 2018/00642* (2013.01); *A61B 2018/00702* (2013.01); *A61B 2018/00761* (2013.01); *A61B 2018/00779* (2013.01); *A61B 2018/00827* (2013.01); *A61B 2018/00875* (2013.01); *A61B 2018/00892* (2013.01); *A61B 2018/1425* (2013.01)

(58) Field of Classification Search
CPC .............. A61B 2018/1425; A61B 2018/00327
See application file for complete search history.

(56) References Cited

U.S. PATENT DOCUMENTS

| | | | |
|---|---|---|---|
| 6,148,232 A | 11/2000 | Avrahami | |
| 6,210,402 B1 | 4/2001 | Olsen et al. | |
| 6,589,235 B2 | 7/2003 | Wong et al. | |
| 6,615,079 B1 | 9/2003 | Avrahami | |
| 8,357,157 B2 | 1/2013 | Mirizzi et al. | |
| 8,496,654 B2 * | 7/2013 | Adanny | A61B 18/14 606/41 |
| 8,579,896 B2 | 11/2013 | Kreindel | |
| 8,936,594 B2 | 1/2015 | Wolf et al. | |
| 9,072,597 B2 | 7/2015 | Wolf et al. | |
| 9,095,357 B2 | 8/2015 | Manstein | |
| 9,108,036 B2 | 8/2015 | Adanny et al. | |
| 9,125,677 B2 | 9/2015 | Sabol et al. | |
| 9,179,967 B2 | 11/2015 | Wolf et al. | |
| 9,237,924 B2 | 1/2016 | Wolf et al. | |
| 9,415,194 B2 | 8/2016 | Wolf et al. | |
| 9,433,463 B2 | 9/2016 | Wolf et al. | |

(Continued)

*Primary Examiner* — Michael F Peffley
*Assistant Examiner* — Samantha M Good
(74) *Attorney, Agent, or Firm* — Allen, Dyer, Doppelt & Gilchrist, P.A.

(57) ABSTRACT

Nasal airway reshaping is accomplished using a fractional treatment device applied externally to the nose to insert needle electrodes into nasal tissue to be reshaped. Energy is applied via the electrodes to cause at least partial coagulation of the nasal tissue within zones around each of the plurality of needle electrodes while pressure is applied internally to achieve the desired reshaping.

12 Claims, 3 Drawing Sheets

(56) References Cited

U.S. PATENT DOCUMENTS

| | | |
|---|---|---|
| 9,452,010 B2 | 9/2016 | Wolf et al. |
| 9,480,836 B2 | 11/2016 | Na |
| 9,486,278 B2 | 11/2016 | Wolf et al. |
| 9,510,899 B2 | 12/2016 | Manstein |
| 9,526,571 B2 | 12/2016 | Wolf et al. |
| 9,687,296 B2 | 1/2017 | Wolf et al. |
| 9,788,886 B2 | 10/2017 | Wolf et al. |
| 9,877,778 B2 | 1/2018 | Manstein |
| 9,888,957 B2 | 2/2018 | Wolf et al. |
| 9,913,682 B2 | 3/2018 | Wolf et al. |
| 10,265,115 B2 | 4/2019 | Wolf et al. |
| 10,398,489 B2 | 9/2019 | Wolf et al. |
| 10,470,814 B2 | 11/2019 | Wolf et al. |
| 10,485,603 B2 | 11/2019 | Wolf et al. |
| 10,603,059 B2 | 3/2020 | Dinger et al. |
| 2008/0125775 A1* | 5/2008 | Morris ............... A61B 18/1477 606/50 |
| 2010/0023003 A1* | 1/2010 | Mulholland ....... A61B 18/1477 606/186 |
| 2017/0231651 A1* | 8/2017 | Dinger ............... A61B 18/1445 604/20 |
| 2019/0336196 A1* | 11/2019 | Wolf ..................... A61B 18/02 |

* cited by examiner

NASAL TISSUE TREATMENT METHOD AND RELATED DEVICE

CROSS-REFERENCE TO RELATED APPLICATION

This application claims the benefit of U.S. Provisional Patent Application Ser. No. 63/054,437, filed on Jul. 21, 2020, the contents of which are herein incorporated by reference in their entirety.

FIELD OF THE INVENTION

The present invention relates to using energy applied via needle electrodes to treat nasal tissue, and more particularly, to methods and devices for reshaping nasal airways using radiofrequency (RF) energy.

BACKGROUND OF THE INVENTION

Fractional treatment devices have become common for skin and subdermal fat treatment. Fractional injuries to the skin and dermis can be delivered by laser systems such as the Fraxel® system made by Reliant Technologies, Inc., which sends small beams of erbium glass laser wavelengths into the dermis, or alternatively by micro-needling, surface ablation or invasive needling. The advantage of delivering segmental, fractional injury is that the tissue is stimulated with an aggressive fractional trauma providing fractional skin resurfacing, skin tightening, acne scar and wrinkle treatment. Fractional treatment devices can also be useful in the treatment of hyperhidrosis and acne, as well as in transdermal drug delivery.

U.S. Pat. No. 6,210,402 describes a method for dermatological treatment of skin by applying high frequency electrical energy to an electrode terminal comprising multiple conductive elements.

U.S. Pat. Nos. 6,148,232 and 6,615,079 describe a method and device for fractional ablation of the stratum corneum for transdermal drug delivery.

U.S. Pat. Nos. 8,357,157 and 8,496,654 describe a device for cosmetic fractional epidermis ablation where multiple electrodes are applied to the skin surface having a grounded return electrode.

U.S. Pat. No. 8,579,896 describes fractional coagulation of skin with electrodes configured not to penetrate the skin.

U.S. Pat. No. 9,108,036 describes a skin treatment device having an applicator tip with a plurality of electrodes configured for contacting a stratum corneum layer for delivering RF energy.

U.S. Pat. No. 9,480,836 describes a needle array for penetrating the skin and powered by motor connecting to the array.

U.S. Pat. No. 9,480,836 describes devices for skin treatment with arrays of insertable needles and RF energy delivered to the needles.

U.S. Pat. Nos. 9,877,778, 9,095,357 and 9,510,899 describe fractional treatment of skin and subdermal fat using a micro-needling RF device.

All these extensive developments for skin treatment are based on the basic idea of coagulating small zones of skin while keeping enough live cells around each zone for fast healing with minimal downtime and without adverse effects. All the above-mentioned inventions are concerned with aesthetic skin treatment.

U.S. Pat. Nos. 8,936,594, 9,072,597, 9,179,967, 9,237,924, 9,415,194, 9,433,463, 9,452,010, 9,486,278, 9,526,571, 9,687,296, 9,788,886, 9,888,957, 9,913,682, 10,265,115, 10,398,489, 10,470,814, 10,485,603 and 10,603,059 describe a method of opening nasal airway by reshaping nasal tissue. The method utilizes a RF probe inserted into the nostril and used to apply RF energy simultaneously with applying mechanical pressure.

The treatment effect is based on a method described in U.S. Pat. Nos. 6,589,235 and 9,125,677, which use RF and laser for cartilage tissue reshaping by heating the tissue up to 60-80° (C.). Such temperature applied to a large surface area would result in cell thermal necrosis and burns. Additionally, delivering energy from within the nostril limits visibility and control of the treatment.

SUMMARY OF THE INVENTION

In view of the foregoing, it is an object of the present invention to apply the advantages of fractional treatment devices to the reshaping of nasal airways in order to minimize unwanted tissue damage, resulting in faster healing, minimal or no downtime, less discomfort, and fewer side effects.

The present invention includes a procedure and method for micro-needling RF treatment of nasal tissue. Aspects of the present invention include applying an applicator having array of electrodes externally to the side of the nose, inserting the array of electrodes into tissue to be treated, reshaping tissue containing cartilage mechanically to a desired new shape, and applying pulse of RF energy to the electrodes to generate a high temperature in the vicinity of each electrode and obtain stress relaxation of the cartilage.

Advantageously the array of electrodes can be designed as micro-needles and a surface of needles can be partially coated with non-conductive material for delivering more RF energy inside the tissue and less energy to the surface layer so as to minimize external thermal damage.

The array of electrodes may comprise two or more conductive elements. Preferably, the array of electrodes includes at least four elements for faster and more effective treatment, and not more than 50 needles to minimize the force of needle insertion into the tissue. Also preferably, the electrodes conical or pyramidal and a length of conductive elements can vary from 0.5 millimeters (mm) up to 10 mm depending on treatment requirements.

A preferred thickness or diameter of the conductive elements is from 0.1 mm up to 0.5 mm. A preferred distance between conductive elements is at least 1 mm. Most preferably, a distance between electrodes with different polarity should be above 1.5-2.5 mm.

The applicator may have a disposable part including the electrodes and a reusable part including more expensive mechanical and electronics elements. Alternatively, the whole applicator can be disposable with less costly elements being used in its construction.

The reusable part can include an electronic or electromechanical component pushing the electrodes into the treated tissue. Alternatively, a simple mechanism operated by user could be used. The mechanism can push the array of electrodes to a fixed distance or to a distance controlled by the user or a processor associated with the device. A distance that electrodes can be pushed out of applicator is preferably in the range of 0.5 mm up to 10 mm. The electrodes can be pushed in radial, axial or any other direction required for the specific treatment. The direction of pushing can be fixed for a specific application or alternatively can be adjustable.

Sharp ends of the electrodes can advantageously be withdrawn completely within the applicator by a reciprocating mechanism allowing scanning of the applicator. Alternatively, a user can simply push needle into the tissue by hand without any reciprocating mechanism.

An RF generator generating alternating electrical voltage with a frequency of 100 kilohertz (kHz) to 40 megahertz (MHz) is advantageously connected to the electrode array. The amount of RF energy should be high enough to coagulate or/and ablate the tissue around the conductive elements but low enough to prevent full thickness tissue burn.

Energy is delivered in a pulsed manner and energy delivery time does not exceed 5 seconds to prevent significant skin conduction. An RF pulse power is preferably varied from 1 watt (W) to 2000 W depending on number of electrodes. RF energy during each pulse can be delivered continuously or with train of shorter RF sub-pulses having higher power. Preferably, RF pulse duration for each electrode can be varied from 10 microseconds (µs) up to 1000 milliseconds (ms). Generally, to achieve a desired thermal effect, with high RF power a shorter pulse is used, and with low RF power a longer pulse is used. The RF energy delivered to each electrode is preferably limited by 5 joules (J) to avoid excessive damage therearound.

The RF energy can be applied between electrodes in the array. Alternatively, the RF energy can be applied between electrodes pushed into the tissue and a return electrode located on the applicator and preferably having larger area a total area of the electrodes. Alternatively, a mono-polar scheme can be used with a large area return electrode placed on the skin surface separately from the applicator.

The RF energy can be applied between one electrode having one polarity and acting as active electrode and all other electrodes having the opposite polarity and collectively functioning as the return electrode. The electrode acting as the active electrode is preferably switched between all the electrodes. If, in each moment of time, only one of the conductive elements acts as the active electrode this allows more accurate measurement of the energy being delivered.

A thermal treatment effect generated around each electrode to cause tissue remodeling can include ablation, coagulation and sub-necrotic heating.

The device powering the applicator can advantageously include a microprocessor controlling the electronics and a user interface. The microprocessor can monitor one or more of: tissue temperature and RF parameters (including but not limited to RF voltage, RF current, RF power, RF impedance, phase shift between RF voltage and RF current). RF power and pulse duration can be adjusted according to measurements to insure uniform and effective treatment. In addition, controller may control and monitor pushing and retraction of conductive elements.

The tissue can be shaped prior the application of RF energy by inserting a cotton tampon into the nostril to expand the air way. Alternatively, a rubber plug can be used. Additionally, special forceps could be used to reshape the tissue during the treatment. Cartilage deformation is preferably maintained during the heating and following cooling process.

The skin surface can be cooled using thermoelectric coolers, cryogen spay or precooled liquid to reduce skin damage. For instance, a part of the applicator applied to the skin surface can be used to cool to prevent skin burn while the electrode array penetrates into the cartilage tissue.

In addition, an inner part of the nose opposite to energy application can be cooled to prevent thermal damage of mucosal layer inside the nostril. The cooling inside the nostril can be done using, for instance, a thermo-electric cooler, forced cold air or cryogen spray. Alternatively, a cotton tampon with a precooled liquid can be used to cool tissue inside the nostril.

The applicator can create cartilage heating using one of more types of energies including, for example, RF energy, ultrasound, optical or microwave energy. RF energy for cartilage heating can be delivered from one or more electrodes applied to the skin surface above treated cartilage tissue. Cartilage shaping can be performed using forceps or compressible materials inserted into the nostril to reshape cartilage prior the energy application.

The method can be applied to treatment of snoring, nasal obstruction and other ear, nose and throat (ENT) applications requiring reshaping cartilage and other collagenous tissue responsible for the shape of the nose and airway.

A method of reshaping a nasal airway according to the present invention includes applying mechanical pressure from inside a nostril to reshape a portion the nasal airway, inserting, to a predetermined depth, a plurality of needle electrodes of a hand piece through an external skin surface of the nose into nasal tissue adjacent to the reshaped portion, and applying a predetermined amount of radiofrequency (RF) energy via the plurality of needle electrodes after insertion to cause at least partial coagulation of the nasal tissue within respective zones around each of the plurality of needle electrodes.

Another method of reshaping a nasal airway according to the present invention includes applying mechanical pressure from inside a nostril to reshape a portion the nasal airway, inserting a plurality of needle electrodes of a hand piece through an external skin surface of the nose into nasal cartilage adjacent to the reshaped portion, applying a predetermined amount of energy via the plurality of needle electrodes after insertion to heat at least a portion of the nasal cartilage above 50° Celsius (C), and cooling nasal mucosa and the external skin surface to prevent thermal damage.

A further method of reshaping a nasal airway according to present invention includes applying mechanical pressure from inside a nostril to reshape a portion the nasal airway, inserting a plurality of needle electrodes of a hand piece through an external skin surface of the nose into nasal cartilage adjacent to the reshaped portion, receiving temperature feedback from the portion of the nasal cartilage, and applying a predetermined amount of radiofrequency (RF) energy via the plurality of needle electrodes after insertion to heat at least a portion of the nasal cartilage according to the temperature feedback to maintain a predetermined temperature for a predetermined time.

These and other objects, aspects and advantages of the present invention will be better appreciated in view of the drawings and following detailed description of preferred embodiments.

DETAILED DESCRIPTION OF PREFERRED EMBODIMENTS

Figure 1:
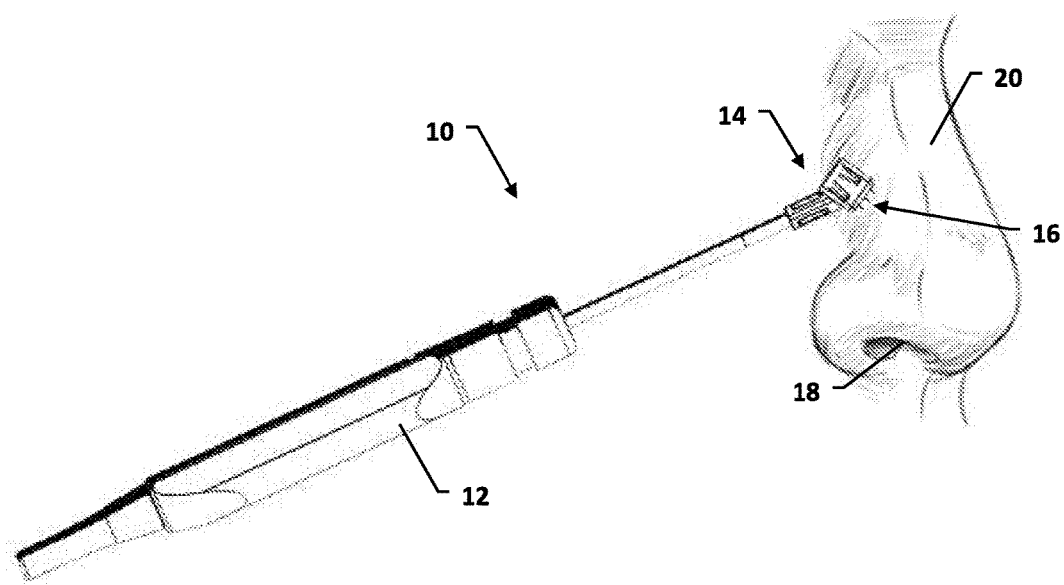
FIG. 1 is a schematic view of an applicator hand piece being applied to an external skin surface of the nose adjacent to nasal tissue to be treated, according to an embodiment of the present invention.
Figure 2:
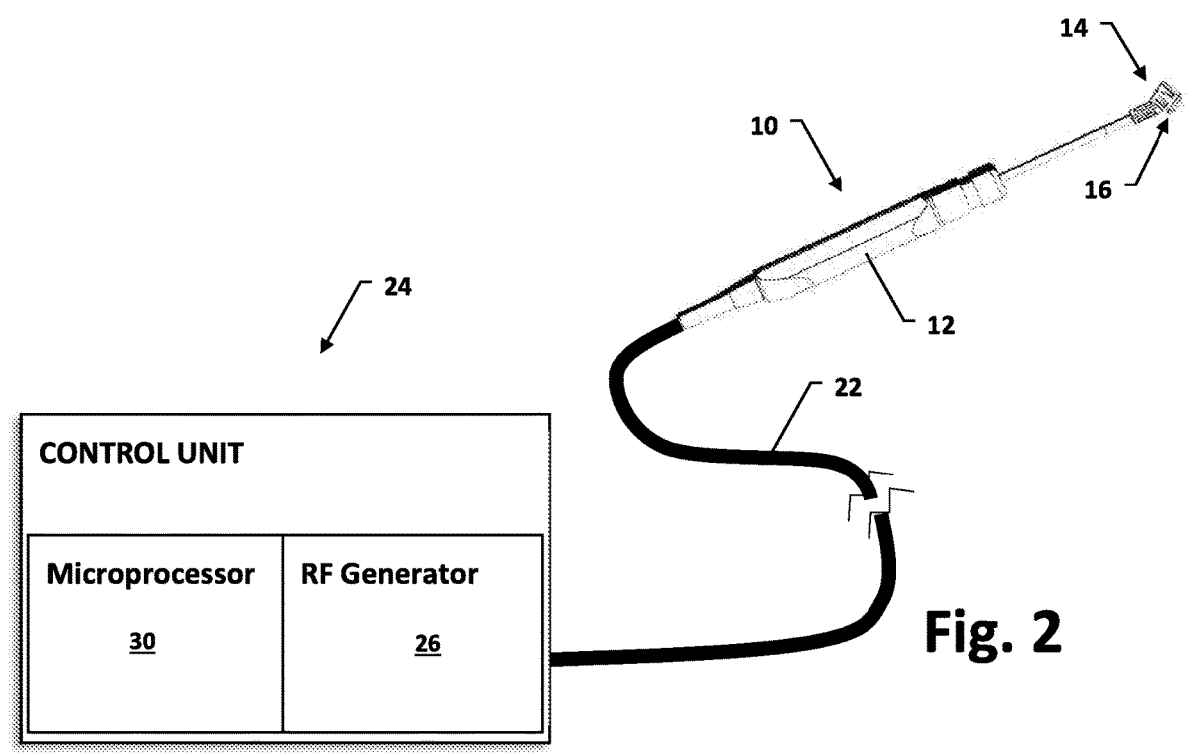
FIG. 2 is a schematic overview of an applicator assembly including the hand piece of FIG. 1 and a connected power source and microprocessor.

Referring first to FIG. 1, an applicator handpiece 10 includes a reusable handle 12 carrying a disposable tip 14 at the distal end with array 16 of electrodes applied to the nose 20. The disposable tip 14 is connected at its proximal end mechanically and electrically to the handle 12. The array 16 of electrodes is located in the distal end of the disposable tip 14. Referring to FIG. 2, the handle is connected via cable 22 to a control unit 24 including an RF generator 26 and a microprocessor 30 controlling the delivery of RF energy to the electrode array 16.

A cotton tampon is inserted into the nostril 18 to reshape the nose and enlarge the airway. The RF energy heats the cartilage tissue inside the nose resulting in cartilage stress relaxation and forming a new shape after cartilage cooling.

Figure 3:
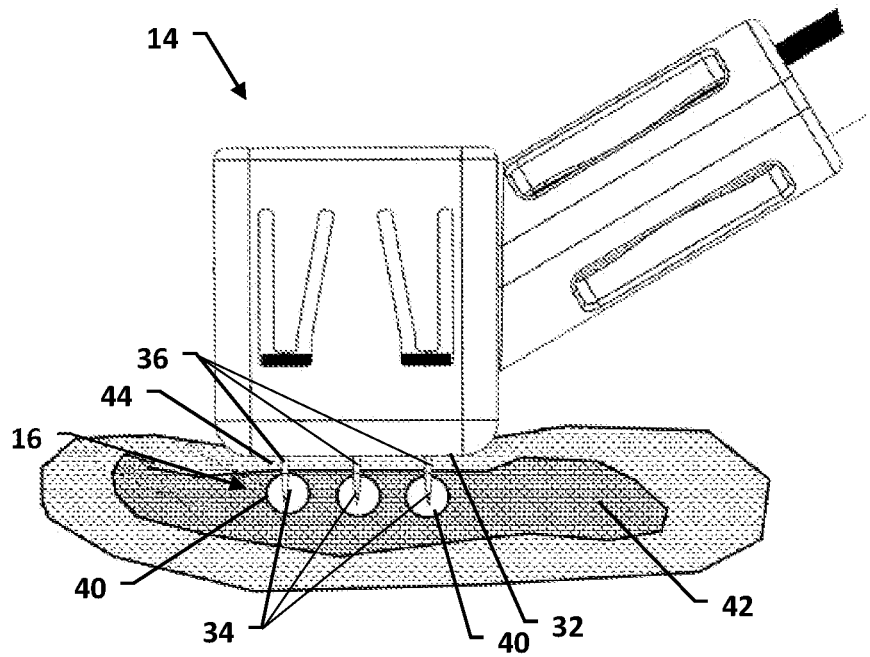
FIG. 3 is a schematic view of the distal end of FIG. 2 with the electrode array applied to the nasal tissue to be treated and a coagulation zone created therein.

Referring to FIG. 3, at the distal end, the tip 14 includes a tissue application surface 32 with electrodes 34 of the electrode array 16 extending therefrom. The electrodes 34 are needle shapes with sharp ends. Upper portions 36 of each electrode 34 can be coated with a polymer to protect the skin surface from thermal damage such that only the uncoated ends deliver RF energy at a predetermined depth.

The applicator contact surface 32 is applied to the treated area with firm pressure allowing the electrodes 34 to penetrate into the tissue to deliver RF energy into the treated volume and create coagulation zones 40 around the un-insulated ends of each electrode 34. The applicator contact surface 32 could also include a return electrode and/or a cooling element.

As seen in FIG. 3, the un-insulated ends of the electrodes 34 only create the coagulation zones 40 inside the cartilage 42 while surface tissue 44 is preserved from thermal damage by insulated upper portions 36. This configuration helps avoid surface thermal damage, reduce the risk of infection and minimize healing time.

Figure 4:
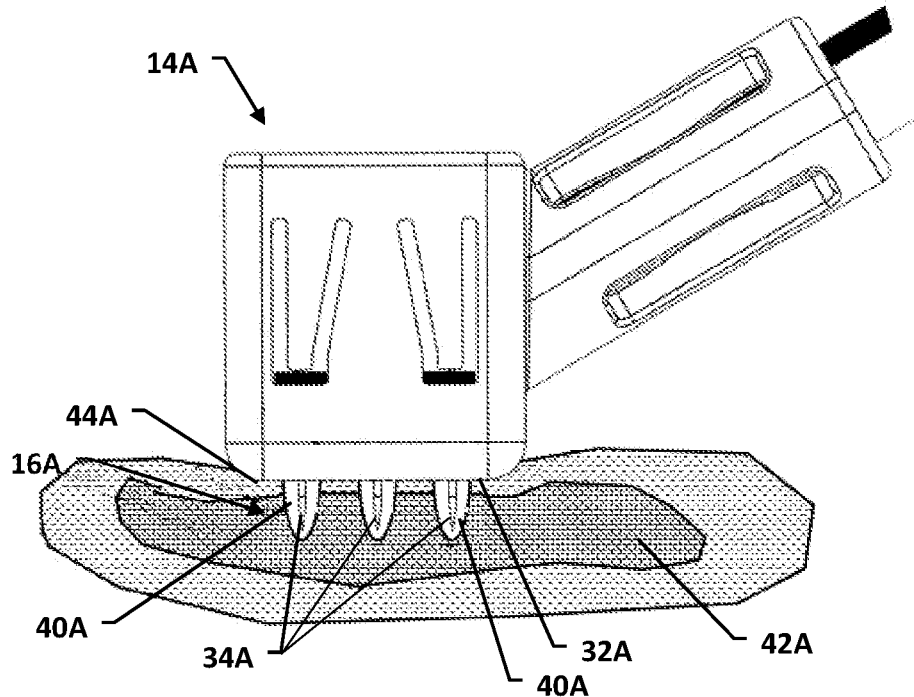
FIG. 4 is a schematic view of another embodiment of the distal end of FIG. 2, with non-insulated electrodes creating coagulation craters therealong.

Referring to FIG. 4, in an alternate embodiment of the tip 14A (with like elements given like reference numbers followed by an "A"), the conductive elements 34A are completely uninsulated. As a result, coagulation craters 40A extend from the cartilage 42A through the surface tissue 44A. This configuration allows the generation of a larger coagulation volume.

Figure 5:
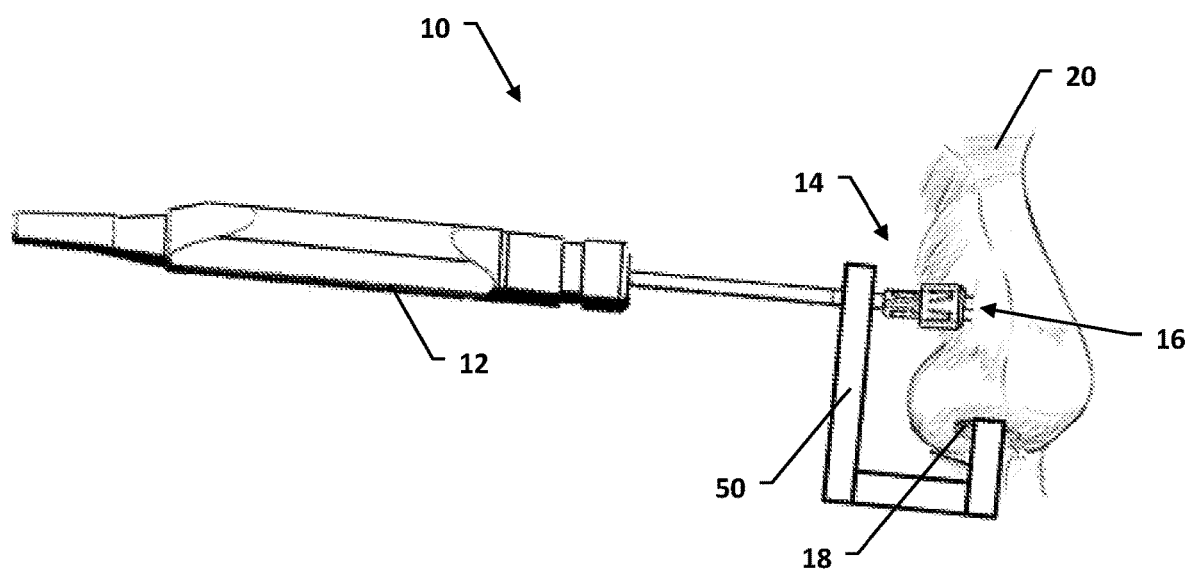
FIG. 5 is a schematic view of the hand piece of FIG. 1, further including a supporting mechanism for reshaping the nasal tissue.

Referring first to FIG. 5, to facilitate reshaping of the nasal airway during treatment, a supporting mechanism 50 can be connected to the handle 12 along with the disposable tip 15. The supporting mechanism 50 is configured such that a distal end thereof extends into the nostril 18 and engages the side of the treated tissue opposite the electrode array 16. Advantageously, the supporting mechanism 50 is used to enlarge the nose opening airway for better breathing.

a. While the present invention is not necessarily limited thereto, preferred parameters applicator handpiece 10 and control unit 24 include:
b. Up to 100 electrodes, but more preferably from 4 to 25 for easier penetration into the tissue and addressing small treatment areas.
c. The average RF energy per electrode is in the range of 10 millijoules (mJ) to 5 J, with a more preferred energy range being from 20 mJ to 1 J per electrode.
d. The penetration depth of the electrodes is from 0.5 mm to 10 mm. The penetration depth can be fixed or adjustable.
e. RF voltage applied to the skin in the range of 10 volts (V) to 1000V.
f. A pulse repetition rate from 0.2 pulses per second (pps) to 2 pps.
g. A cotton tampon, rubber plug or special mechanical inserted into the nostril is used to expand nasal airway prior to and during the energy application.

In general, the foregoing description is provided for exemplary and illustrative purposes; the present invention is not necessarily limited thereto. Rather, those skilled in the art will appreciate that additional modifications, as well as adaptations for particular circumstances, will fall within the scope of the invention as herein shown and described and of the claims appended hereto.

What is claimed is:

1. A method of reshaping a nasal airway, the method comprising:
   applying mechanical pressure from inside a nostril to reshape a portion the nasal airway;
   inserting, to a predetermined depth, a plurality of needle electrodes of a hand piece through an external skin surface of the nose into nasal tissue adjacent to the reshaped portion; and
   applying a predetermined amount of radiofrequency (RF) energy via the plurality of needle electrodes after insertion to cause at least partial coagulation of the nasal tissue within respective zones around each of the plurality of needle electrodes;
   wherein a portion of each of the plurality of needle electrodes is coated with an insulating material to minimize application of RF energy adjacent to the portion; and
   wherein each portion is closer to the hand piece than a remaining, uninsulated portion of each of the plurality of needle electrodes.

2. The method of claim 1, wherein a length of each of the plurality of needle electrodes is from 0.5 millimeters (mm) to 10 mm.

3. The method of claim 1, wherein at least four needle electrodes are inserted into the nasal tissue.

4. The method of claim 1, wherein applying the predetermined amount of RF energy includes applying the RF energy in at least one pulse having a duration of 1 millisecond to 5 seconds.

5. The method of claim 1, wherein applying the predetermined amount of RF energy via the plurality of needle electrodes includes using at least one of the plurality of needle electrodes as at least one active electrode, with a remainder of the plurality of needles electrodes being return electrodes.

6. The method of claim 5, wherein using the least one of the plurality of needle electrodes as at least one active electrode includes using only one of the plurality needle electrodes as only one active electrode.

7. The method of claim 6, wherein using only one of the plurality needle electrodes as only one active electrode includes switching which of the plurality of needle electrodes is the only one active electrode.

8. The method of claim 1, wherein applying the predetermined amount of RF energy via the plurality of needle electrodes includes using at least one of the plurality of needle electrodes as at least one active electrode and using a surface electrode applied to the external skin surface as a return electrode.

9. The method of claim 1, wherein applying the predetermined amount of RF energy via the plurality of needle electrodes is performed such that each of the respective zones is smaller than a distance between adjacent ones of the plurality of needle electrodes.

10. The method of claim 1, wherein applying the predetermined amount of RF energy via the plurality of needle electrodes includes:
   measuring at least one parameter during application of the RF energy, the at least one parameter including at least one of RF current, RF voltage, RF power and tissue impedance during application of the RF energy; and
   adjusting RF power and pulse duration according to the at least one parameter.

11. The method of claim 1, further comprising cooling nasal mucosa and the external skin surface while applying the predetermined amount of RF energy.

12. A method of reshaping a nasal airway, the method comprising:
   applying mechanical pressure from inside a nostril to reshape a portion the nasal airway;
   inserting, to a predetermined depth, a plurality of needle electrodes of a hand piece through an external skin surface of the nose into nasal tissue adjacent to the reshaped portion; and
   applying a predetermined amount of radiofrequency (RF) energy via the plurality of needle electrodes after insertion to cause at least partial coagulation of the nasal tissue within respective zones around each of the plurality of needle electrodes;
   wherein applying the predetermined amount of RF energy includes pulsed application of the RF energy with a pulse duration of 1 millisecond to 5 seconds.

* * * * *